(12) United States Patent
Wieters

(10) Patent No.: US 11,675,159 B2
(45) Date of Patent: Jun. 13, 2023

(54) PRISM HOLDER OF A SURGICAL INSTRUMENT, AND SURGICAL INSTRUMENT

(71) Applicant: OLYMPUS WINTER & IBE GMBH, Hamburg (DE)

(72) Inventor: Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 446 days.

(21) Appl. No.: 16/830,441

(22) Filed: Mar. 26, 2020

(65) Prior Publication Data

US 2020/0225446 A1 Jul. 16, 2020

Related U.S. Application Data

(63) Continuation of application No. PCT/EP2018/074623, filed on Sep. 12, 2018.

(30) Foreign Application Priority Data

Sep. 26, 2017 (DE) .......................... 102017122279.0

(51) Int. Cl.
*G02B 7/18* (2021.01)
*A61B 1/00* (2006.01)
*A61B 1/05* (2006.01)

(52) U.S. Cl.
CPC ........ *G02B 7/1805* (2013.01); *A61B 1/00066* (2013.01); *A61B 1/00096* (2013.01); *A61B 1/00147* (2013.01); *A61B 1/00183* (2013.01); *A61B 1/05* (2013.01)

(58) Field of Classification Search
CPC .......... G02B 7/18; G02B 7/1805; G02B 5/04; G02B 23/2423; G02B 13/0065; G02B 17/086; G02B 23/02; G02B 27/646; H04N 5/2254; A61B 1/05; A61B 1/051; A61B 1/053
See application file for complete search history.

(56) References Cited

U.S. PATENT DOCUMENTS

| 2,400,401 | A | 5/1946 | Eckerman et al. |
| 4,727,859 | A | 3/1988 | Lia |
| 2001/0001252 | A1 | 5/2001 | Umetsu |

(Continued)

FOREIGN PATENT DOCUMENTS

| CN | 102884470 A | 1/2013 |
| DE | 269461 | 6/1989 |

(Continued)

OTHER PUBLICATIONS

International Search Report dated Nov. 22, 2018 issued in PCT/EP2018/074623.

*Primary Examiner* — Alexandra L Newton
(74) *Attorney, Agent, or Firm* — Scully, Scott, Murphy & Presser, P.C.

(57) ABSTRACT

A prism holder for use with a surgical instrument, having a prism. The prism holder including: a casing for receiving the prism; and at least one prism pressure element configured to be brought into contact with a pressure surface of the prism; wherein the casing having an opening for arrangement of the at least one prism pressure element in the opening.

17 Claims, 3 Drawing Sheets

(56) References Cited

U.S. PATENT DOCUMENTS

| | | | | |
|---|---|---|---|---|
| 2012/0182458 A1* | 7/2012 | Ishii | ................. | H04N 5/2254 |
| | | | | 359/833 |
| 2013/0120647 A1 | 5/2013 | Negishi | | |
| 2016/0345805 A1 | 12/2016 | Wieters et al. | | |
| 2017/0131529 A1* | 5/2017 | Lu | ................. | G02B 7/1805 |

FOREIGN PATENT DOCUMENTS

| | | |
|---|---|---|
| DE | 102014202669 A1 | 8/2015 |
| EP | 2369395 A1 | 9/2011 |
| EP | 2 494 909 A1 | 9/2012 |
| EP | 2568324 A1 | 3/2013 |
| JP | S61-49320 U | 4/1986 |
| JP | 2007-041121 A | 2/2007 |
| JP | 2007-094359 A | 4/2007 |
| JP | 2014-119474 A | 6/2014 |
| WO | 2011/027594 A1 | 3/2011 |

\* cited by examiner

PRISM HOLDER OF A SURGICAL INSTRUMENT, AND SURGICAL INSTRUMENT

CROSS-REFERENCE TO RELATED APPLICATION

The present application is a continuation of PCT/EP2018/074623 filed on Sep. 12, 2018, which is based upon and claims the benefit to DE 10 2017 122 279.0 filed on Sep. 26, 2017, the entire contents of each of which are incorporated herein by reference.

BACKGROUND

Field

The present disclosure relates to a prism holder of a surgical instrument, and more particularly to an endoscope, such as a video endoscope, for at least one surgical instrument having a prism. The present disclosure additionally relates to a surgical instrument, and more particularly to an endoscope.

Prior Art

Various embodiments of endoscopes, such as video endoscopes, in which the light of an operating field entering at a distal tip of an endoscope shaft of the endoscope is conducted through an optical system to a proximal eyepiece or to one or more image sensors, are known. There are thus endoscopes which look forward, which have a so-called 0° viewing direction, or endoscopes having a lateral viewing direction, which have for example a lateral viewing direction of 30°, 45°, 70° or similar deviating from the 0° viewing direction. The numbers of degrees indicated denote the polar angle between the central visual axis and the longitudinal axis of the endoscope shaft. There also exist endoscopes or respectively video endoscopes having an adaptable lateral viewing direction, in which the viewing angle, that is to say the deviation from looking forward, can be adjusted. In addition to adjusting the viewing angle, that is to say the deviation from looking forward, the viewing direction, that is to say the azimuth angle, can also be adjusted around the longitudinal axis of the endoscope shaft by rotating the endoscope as a whole around the longitudinal axis of the endoscope shaft.

In EP 2 369 395 A1, an optical system for a video endoscope is shown, in which the viewing angle is altered in that a first prism of a prism group having three prisms arranged distally in the endoscope shaft is rotated or respectively swiveled around a rotational axis which is located perpendicularly or respectively transversely to the longitudinal axis of the endoscope shaft. This first prism is also referred to as a swiveling prism. The other two prisms, which define the optical beam path together with the first prism, are bonded to one another and are not co-rotated.

The prisms are ground from glass blocks. The width of the respective glass block is governed by the size of the beam path. The swiveling prism is received in a swiveling prism holder and is positioned by three stop surfaces. The swiveling prism holder itself is rotatably mounted in a holding device. The alignment of the prism, such as to the rotational axis thereof, is very important in the design and production of appropriate prism groups or prism sets.

A prism holder arrangement for an endoscope having a variable viewing direction is additionally known from DE 10 2014 202 669 A1.

In addition, it is known that the image acquirer or respectively image sensor is not arranged vertically, but horizontally to the endoscope shaft axis in video endoscopes. To this end, the image sensor is affixed to a deflection prism, wherein the light inlet surface of the prism is arranged perpendicularly and the light outlet surface of the prism is arranged parallel to the endoscope axis. In this case, it is provided that the deflection prism is fastened in a prism holder using adhesive compound.

SUMMARY

Starting from this prior art, an object consists of improving the positinning and alignment of a prism of an endoscope in a simple manner.

Such object can be achieved by a prism holder of a surgical instrument, such as an endoscope, including a video endoscope, for at least one surgical instrument having a prism, having a casing for receiving a prism, wherein at least one prism pressure element is provided which is or can be brought into contact with a pressure surface of a prism that is or can be arranged in the casing, wherein the casing has a respective opening for the prism pressure element for the prism pressure elements and the at least one prism pressure element is or can be arranged in the respective opening.

The prism pressure element can be brought into contact with the pressure surface selectively, i.e. with a small area of contact so that pressure is applied by means of the prism pressure element against a pressure surface of the prism holder for the prism, wherein the prism can be freely aligned by virtue of the selective contact surface between the prism pressure element and the prism. In this case, a pressing force is applied to the prism in the direction of the locating surface or respectively alignment surface of the holder for the prism by means of the prism pressure element or multiple prism pressure elements. Multiple prism pressure elements can be provided so that multiple pressure surfaces of the prism can be respectively brought into contact with at least one respective prism pressure element.

If, for example, a prism has two pressure surfaces arranged perpendicularly to one another, a respective prism pressure element can be brought into contact with a respective pressure surface so that the prism is pressed by virtue of the forces aligned vertically to one another against locating surfaces or alignment surfaces of the casing which are aligned vertically to one another. The alignment surfaces are respectively arranged perpendicularly to one another.

In an embodiment, the prism pressure element can have a rounded or curved contact surface facing the pressure surface of the prism. As a result, it is possible that a force is applied to the prism by means of a selective contact between the prism pressure element and the pressure surface.

The prism pressure element can be configured as a ball, such as a metal ball, glass ball or a ceramic ball.

The respective opening for the prism pressure element can be configured as a bore in the casing. The opening or bore can be arranged opposite an alignment surface of the prism holder for the prism in the casing.

When a prism is arranged in the casing, the prism pressure element can be fastened, such as by being bonded, in the opening for the prism pressure element. Between an alignment surface against which the prism is pressed, adhesive is not necessary between the alignment surface and the side of the prism facing the alignment surface. The opening or respectively bore for the respective prism pressure element can have a slightly larger diameter than the diameter of the prism pressure element or respectively the ball configured as a prism pressure element for the prism.

Moreover, when a prism is arranged in the casing, the prism pressure element can be connected, such as by being bonded, to the pressure surface of the prism facing the prism pressure element. The prism pressure element or the prism pressure elements or respectively the balls can become bonded in the condition subjected to force when the prism is arranged in the casing, wherein the prism pressure element or the prism pressure elements act as an adhesive gap bridge. The adhesive gap fixing the prism pressure element or respectively the ball between the prism pressure element and the opening or respectively bore can be configured in a circumferential manner around the ball, such as perpendicularly to the adhesive gap between the prism and the prism holder.

In the case of the prism holder, two prism pressure elements can be provided for a respective pressure surface of the prism, as a result of which a simple, precise and inexpensive positioning of the prism in the casing of the prism holder can be achieved.

The prism can be configured as a deflection prism, such as a 90° prism.

In addition, it is provided in an embodiment of the prism holder that the prism can have a cuboid section having two respective pressure surfaces arranged perpendicularly to one another for a respective prism pressure element.

According to a further embodiment, a prism having a light inlet surface and a light outlet surface can be arranged in the casing, wherein the light inlet surface of the prism is aligned perpendicularly to the longitudinal axis of the casing and the light outlet surface of the prism is aligned parallel to the longitudinal axis of the casing.

An image sensor can be arranged in the casing, wherein the image sensor is arranged parallel to the light outlet surface of the prism.

Such object can be additionally achieved by a surgical instrument, such as an endoscope, having a prism holder as described above. To avoid repetitions, reference is expressly made to the previous explanations.

It is furthermore provided that the surgical instrument can have a shaft, such as an endoscope shaft, which can be introduced into a body cavity of a living creature, wherein the prism holder is arranged in the shaft, such as the endoscope shaft. The surgical instrument can be configured as a video endoscope.

Further features will become evident from the description of embodiments, together with the claims and the appended drawings. Embodiments can fulfil individual features or a combination of several features.

BRIEF DESCRIPTION OF THE DRAWINGS

The embodiments will be described below without limiting the general concept of the invention by means of exemplary embodiments with reference to the drawings, wherein reference is expressly made to the drawings regarding all of the details which are not explained in greater detail in the text, wherein.

In the drawings, the same or similar elements and/or parts are, in each case, provided with the same reference numerals so that they are not introduced again in each case.

DETAILED DESCRIPTION

Figure 1:
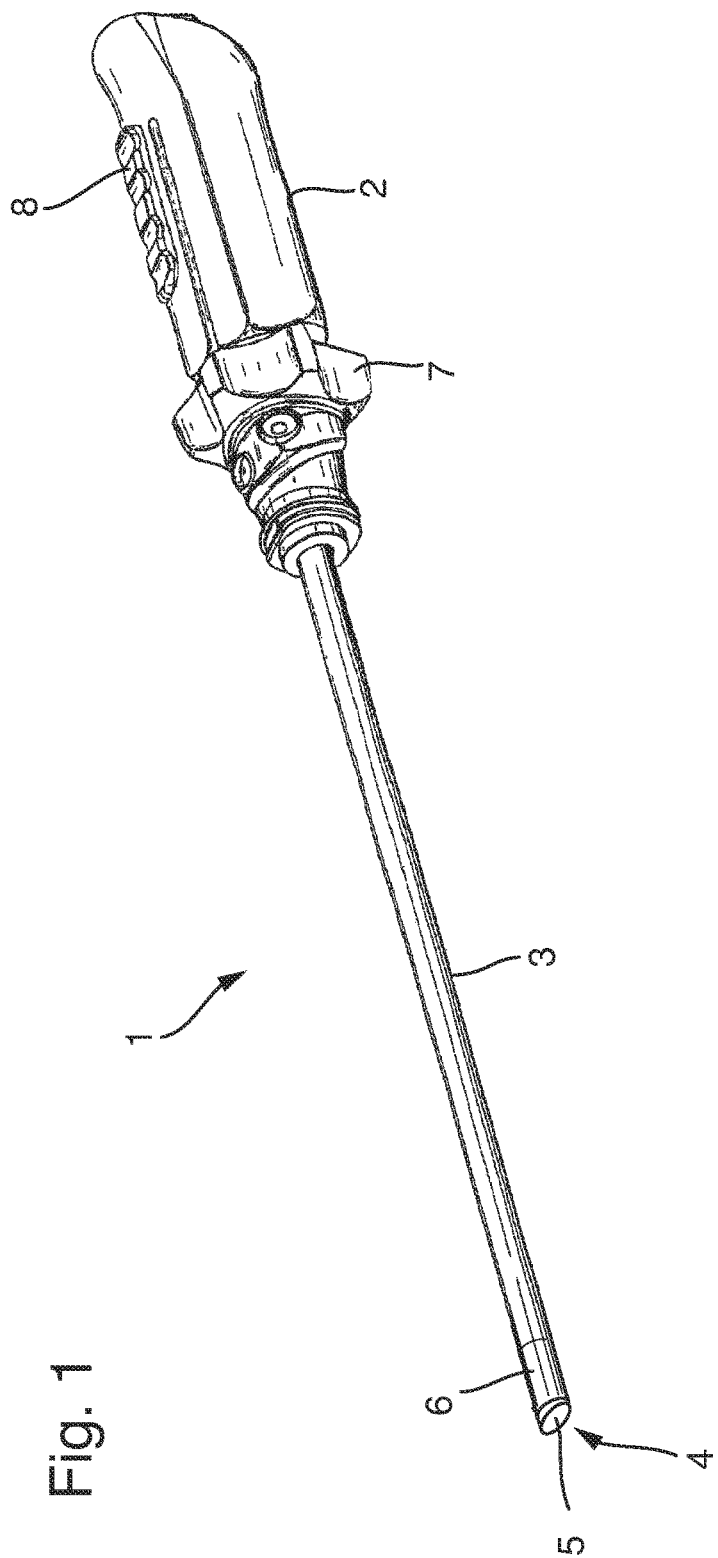
FIG. 1 illustrates a schematic, perspective diagram of an endoscope.

FIG. 1 shows a schematic perspective diagram of an endoscope 1 having a proximal handle 2 and a rigid endoscope shaft 3. At the distal tip 4 of the endoscope shaft 3, an inspection window 5 is arranged, behind which a distal section 6 of the endoscope shaft is arranged, which has a prism unit which is not represented and an image sensor unit which is not represented. The endoscope 1 can be configured as a video endoscope.

The inspection window 5 at the distal tip 4 has a curved and asymmetric design. Therefore, the inspection window 5 is configured to support a variable lateral viewing angle. An alteration of the viewing direction, that is to say an alteration of the azimuth angle around the longitudinal axis of the endoscope shaft 3, is brought about by rotating the handle 2 around the central rotational axis or respectively the longitudinal axis of the endoscope shaft 3. The casing tube of the endoscope shaft 3 is connected to the handle. The prism unit at the distal tip 4, which is not represented, co-rotates with the rotation of the handle 2.

The handle 2 has a first operating element which is configured as a rotating wheel 7 and a second operating element which is configured as a slide 8.

In order to maintain the horizontal location of the displayed image, the rotating wheel 7 is held firmly during a rotation of the handle 2. The result of this is that the image sensor in the interior of the endoscope shaft 3 does not execute the movement as well.

In order to modify the viewing angle, that is to say the deviation of the viewing direction from looking forward, the slide 8 is moved. A sliding of the slide 8 distally leads, for example, to an enlargement of the viewing angle, a retraction of the slide 8 proximally brings about, in this case, a reduction of the viewing angle until the endoscope is looking forward. The actuation of the slide 8 is associated with a rotation of the image sensor, in order to retain the horizontal position of the displayed image even when the prism unit is twisted against one another.

Figure 2:
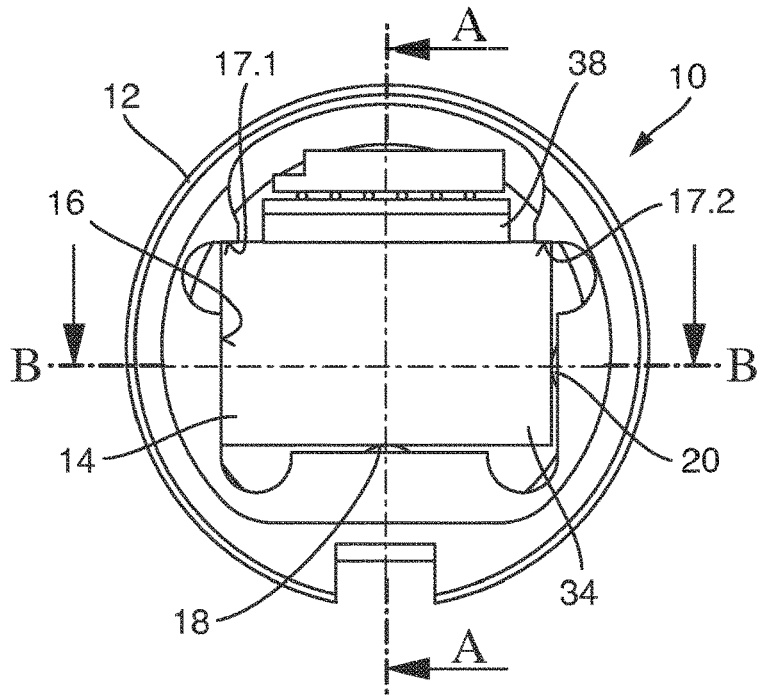
FIG. 2 schematically illustrates a front view of a prism holder for an endoscope.

In FIG. 2 a front view of a prism holder 10 for an endoscope is schematically shown. The prism holder 10 has a casing 12, which can be or is arranged in an endoscope shaft 3 of an endoscope 1. The casing 12 has a hollow space for receiving a prism 14 in the interior. In this case, the casing 12 has multiple stop surfaces 16, 17.1, 17.2 for the prism 14 in the interior, so that the one side surface of the prism 14 is pressed against the stop surface 16 and, at the same time, the upper side of the prism 14 is pressed against the stops 17.1, 17.2 of the casing 12. The stops 17.1, 17.2 are, in this case, arranged in a plane or respectively alignment plane, which is configured perpendicularly to the plane or respectively alignment plane having the stop 16.

In order to press the upper side of the prism 14 against the stops 17.1, 17.2, a pressure ball 18 is provided on the opposite side below the prism 14 and is received in the casing, which pressure ball is in contact with the underside of the prism 14. In this case, the pressure ball 18 contacts the underside and presses the prism 14 against the stops 17.1, 17.2. In addition, in order to position the prism 14 in the casing 12, a further pressure ball 20 is provided laterally, so that the prism 14 is pressed laterally against the stop 16 by means of the pressure ball 20, which presses on the side opposite the stop 16 against a corresponding pressure surface of the prism 14.

Figure 3A:
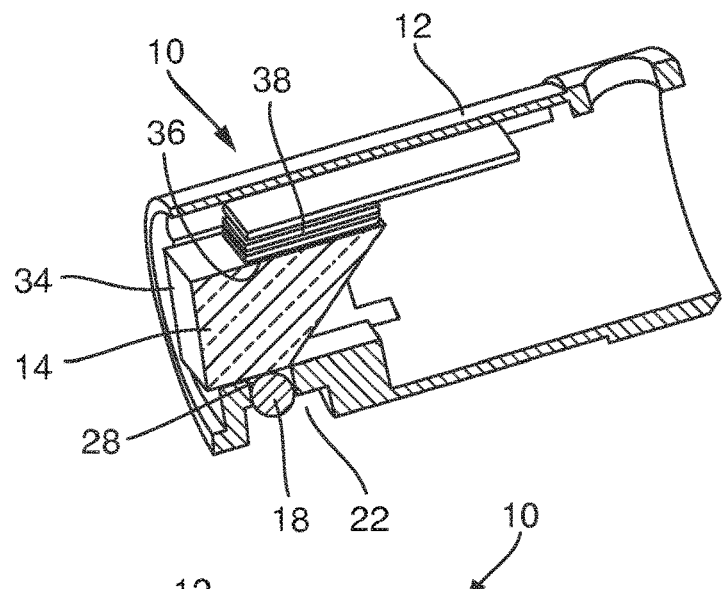
FIG. 3A schematically illustrates a longitudinal section through the prism holder according to the section line A-A represented in FIG. 2.
Figure 3B:
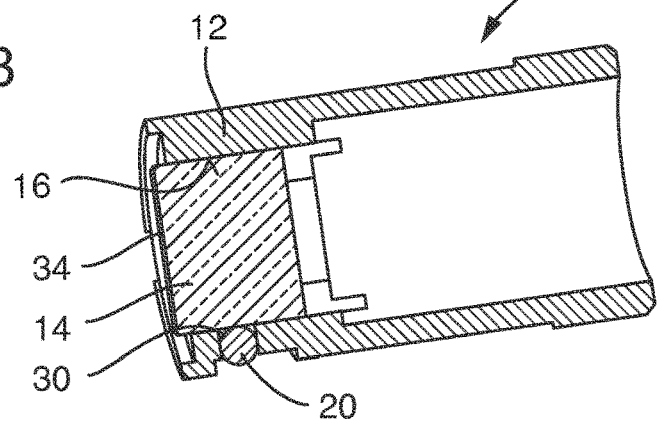
FIG. 3B schematically illustrates a longitudinal section through the prism holder according to the section line B-B represented in FIG. 2.

A longitudinal section through the casing 12 of the prism holder 10 according to the section line A-A represented in FIG. 2 is represented in FIG. 3A. FIG. 3B shows a section through the prism holder 10 according to the section line B-B marked in FIG. 2.

As is clear from FIG. 3A, the casing 12 has a recess 22 on the underside, thus making easier accessibility to the underside to a bore 28 for the pressure ball 18 possible. In order to bring the pressure ball 18 into contact with the underside of the prism 14, a pressure ball 18 is received in the bore 28 in the casing 12.

The prism 14 is pressed from the underside against the stops 17.1, 17.2 on the upper side by means of the pressure ball 18, wherein thanks to the pressure ball 18 it is achieved that a force is applied selectively to the prism 14. After introducing the prism 14 into the prism holder 10, adhesive is applied, in a configuration, through the bore 28 on the underside of the prism 14 and the pressure ball 18, wherein the pressure ball 18 is subsequently introduced. In order to align the prism 14, the pressure ball 18 is subjected to a force so that the upper side of the prism 14 is pressed against the stops 17.1, 17.2. The pressure ball 18 is subsequently bonded to the casing 12 and the prism 14.

As can be seen from FIG. 3B, in order to receive the pressure ball 20, the casing 12 has a bore 30 for the pressure ball 20 so that when the prism 14 is arranged in the casing 12, the lateral pressure surface of the prism 14 is brought into contact with the pressure ball 20 and the prism 14 is pressed against the stop 16 by means of the pressure ball 20. In order to fix the prism 14, the pressure ball 20 is bonded by introducing an adhesive compound over the selective contact surface with the prism 14 and with the casing 12 in the bore 30.

The prism 14 is configured as a deflection prism having a cuboid section, wherein the light inlet side 34 is arranged in a perpendicular plane to the longitudinal axis of the endoscope shaft 3. The cuboid section of the prism 14 has appropriate pressure surfaces which respectively face the pressure balls 18, 20.

The deflection prism 14 additionally has a light outlet side 36, wherein the light outlet side 36 is aligned in a plane parallel to the longitudinal axis of the endoscope 1. An image sensor 38 is arranged on the light outlet side 36 of the prism 14 so that the beams of light rerouted by the deflection prism 14 are captured by means of the image sensor 38. The image sensor 38 can be affixed on the light outlet side 36.

Figure 4A:
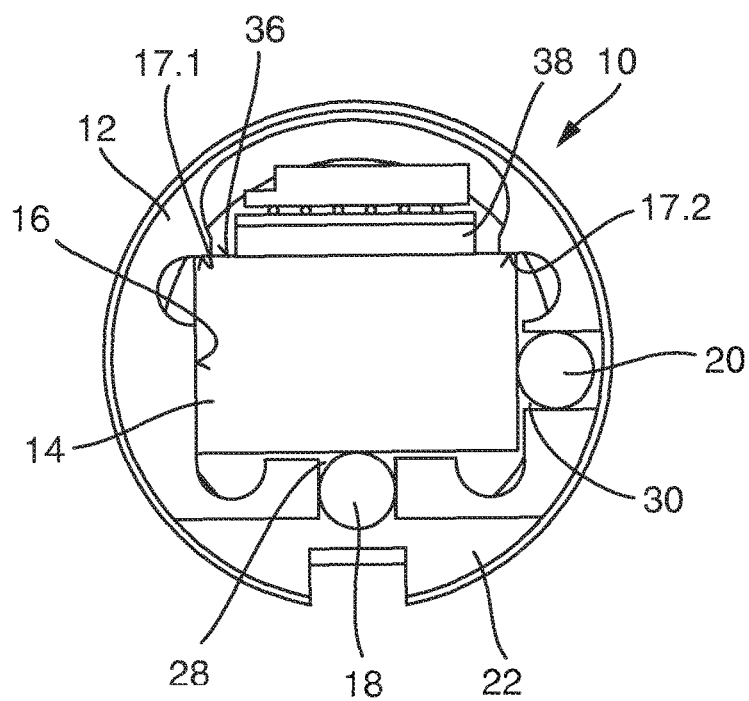
FIG. 4A schematically illustrates a cross-section through the prism holder.
Figure 4B:
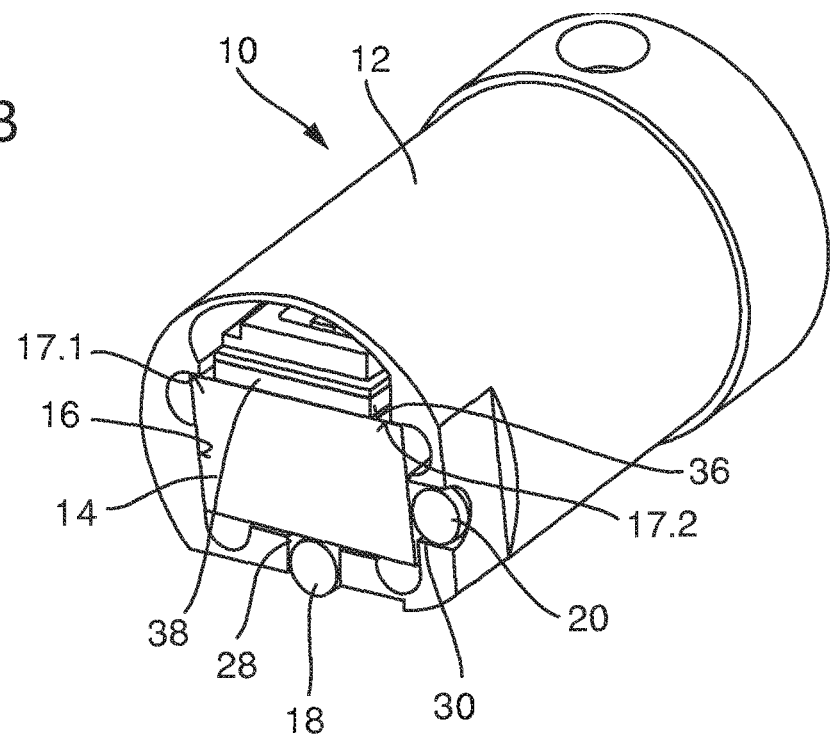
FIG. 4B schematically illustrates a perspective diagram of the prism holder with a cross-sectional diagram.

A cross-section through the casing 12 is schematically represented in the region of the pressure balls 18, 20 in FIG. 4A. FIG. 4B schematically shows a perspective view having the cross-sectional diagram in the region of the pressure balls 18, 20.

As can be seen from both figures, the pressure balls 18, 20 are in contact with the pressure surfaces of the prism 14 which face them, wherein in order to position and fix the prism 14 in the casing 12, the pressure balls 18, 20 are respectively bonded to the facing pressure surface of the prism 14, such as selectively. In order to fix the pressure balls 18, 20 in the respective bores 28, 30, adhesive is likewise introduced into the bores 28, 30 so that, following hardening of the adhesive, the pressure balls 18, 20 are fixed in the bores 28, 30.

In a configuration, the pressure balls 18, 20 can be produced from glass or ceramic.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

1 Endoscope
2 Handle
3 Endoscope shaft
4 Distal tip
5 Inspection window
6 Distal section
7 Rotating wheel
8 Slide switch
10 Prism holder
12 Casing
14 Prism
16 Stop
17.1, 17.2 Stop
18 Pressure ball
20 Pressure ball
22 Recess
28 Bore
30 Bore
34 Light inlet side
36 Light outlet side
38 Image sensor

The invention claimed is:

1. A prism holder for use with a surgical instrument, the prism holder comprising:
    a casing for receiving a prism; and
    first and second prism pressure elements configured to contact with first and second pressure surfaces, respectively, of the prism, the first and second pressure surfaces of the prism being perpendicular to each other;
    wherein the casing having first and second openings formed in a wall of the casing for receiving the first and second prism pressure elements, respectively, in the first and second openings;
    wherein each of the first and second prism pressure elements has a rounded or curved contact surface configured to be in point contact with the first and second pressure surfaces, respectively, of the prism.

2. The prism holder according to claim 1, wherein each of the first and second prism pressure elements are configured as an at least partial sphere separately formed from the casing.

3. The prism holder according to claim 2, wherein each of the first and second prism pressure elements are formed from a material different from a material of the casing.

4. The prism holder according to claim 1, wherein the each of the first and second openings is configured as a bore in the wall of the casing.

5. The prism holder according to claim 1, each of the first and second prism pressure elements are fastened in the first and second openings, respectively, so as to contact with the first and second pressure surfaces, respectively, of the prism.

6. The prism holder according to claim 5, further comprising an adhesive for fastening each of the first and second prism pressure elements in the first and second openings, respectively.

7. The prism holder according to claim 1, wherein each of the first and second prism pressure elements are connected to the first and second pressure surfaces, respectively, of the prism.

8. The prism holder according to claim 7, further comprising an adhesive for fastening each of the first and second prism pressure elements to the first and second pressure surfaces, respectively, of the prism.

9. The prism holder according to claim 1, further comprising the prism, wherein the prism is configured as a deflection prism.

10. The prism holder according to claim 9, wherein the deflection prism is a 90° deflection prism.

11. The prism holder according to claim 1, further comprising the prism, wherein the prism comprises a light inlet surface and a light outlet surface, the light inlet surface of the prism is aligned perpendicularly to a longitudinal axis of the casing and the light outlet surface of the prism is aligned parallel to the longitudinal axis of the casing.

12. The prism holder according to claim 11, further comprising an image sensor arranged in the casing, wherein the image sensor is arranged parallel to the light outlet surface of the prism.

13. The prism holder according to claim 1, wherein the casing further comprising first and second stops, positioned so as to be opposed to the first and second pressure elements, respectively, such that the first and second pressure elements urge the prism against the first and second stops, respectively, when the first and second pressure elements are brought into contact with the first and second pressure surfaces, respectively.

14. A surgical instrument comprising a prism holder according to claim 1.

15. The surgical instrument according to claim 14, further comprising a shaft configured to be introduced into a body cavity wherein the prism holder is arranged in the shaft.

16. The prism holder according to claim 2, wherein one or more of the first and second prism pressure elements are configured as a full sphere.

17. The prism holder according to claim 3, wherein the material is selected from a group consisting of metal, glass and ceramic.

* * * * *